US012070747B2

(12) United States Patent
Carmona-Fontaine

(10) Patent No.: US 12,070,747 B2
(45) Date of Patent: Aug. 27, 2024

(54) DISCRETE MICROENVIRONMENT CHAMBER

(71) Applicant: NEW YORK UNIVERSITY, New York, NY (US)

(72) Inventor: Carlos Carmona-Fontaine, Brooklyn, NY (US)

(73) Assignee: New York University, New York, NY (US)

( * ) Notice: Subject to any disclaimer, the term of this patent is extended or adjusted under 35 U.S.C. 154(b) by 192 days.

(21) Appl. No.: 17/554,369

(22) Filed: Dec. 17, 2021

(65) Prior Publication Data

US 2022/0193660 A1 Jun. 23, 2022

Related U.S. Application Data

(60) Provisional application No. 63/127,485, filed on Dec. 18, 2020.

(51) Int. Cl.
*B01L 3/00* (2006.01)
*C12M 3/06* (2006.01)
*C12N 5/09* (2010.01)

(52) U.S. Cl.
CPC .......... *B01L 3/5027* (2013.01); *C12M 23/16* (2013.01); *C12N 5/0693* (2013.01); *B01L 2200/0647* (2013.01)

(58) Field of Classification Search
None
See application file for complete search history.

(56) References Cited

U.S. PATENT DOCUMENTS

| 2011/0201099 A1* | 8/2011 | Anderson | G01N 1/10 422/68.1 |
| 2015/0247112 A1* | 9/2015 | Orr | C12M 29/10 435/395 |
| 2018/0369820 A1* | 12/2018 | Kaneko | C12M 23/08 |

OTHER PUBLICATIONS

Carmona-Fontaine et al., Metabolic origins of spatial organization in the tumor microenvironment, PNAS, vol. 114, No. 11 (Year: 2017).*

(Continued)

*Primary Examiner* — Maris R Kessel
*Assistant Examiner* — Mickey Huang
(74) *Attorney, Agent, or Firm* — Riverside Law LLP

(57) ABSTRACT

The present invention provides a discrete microenvironment chamber (DIMIC) configured to accurately mimics the microenvironment of poorly perfused tissue. In one embodiment, the DIMIC of the present invention is further designed to allow the extraction of cells and media from different local environments for any type of biochemical analysis.

17 Claims, 11 Drawing Sheets

(56) References Cited

OTHER PUBLICATIONS

Cui et al., A microfluidic device for isolation and characterization of transendothelial migrating cancer cells, Biomicrofluidics 11, 014105 (2017) (Year: 2017).*
Carmona-Fontaine et al., Emergence of spatial structure in the tumor microenvironment due to the Warburg effect, PNAS, vol. 110, No. 48 (Year: 2013).*
Agorku et al., Isolation and analysis of tumor cells from human solid tumor tissue extracted by needle biopsy, Miltenyi Biotec (Year: 2017).*
Microplate Dimensions, Working Volumes and Packaging, 2019, Perkin Elmers (Year: 2019).*
Cochran et al., Evolution of Oxygen and Glucose Concentration Profiles in a Tissue-Mimetic Culture System of Embryonic Stem Cells, vol. 34, pp. 1247-1258, (2006) (Year: 2006).*
Anandi, Libi et al., Direct visualization of emergent metastatic features within an ex vivo model of the tumor microenvironment, bioRxiv (Apr. 28, 2023). Preprint.

* cited by examiner

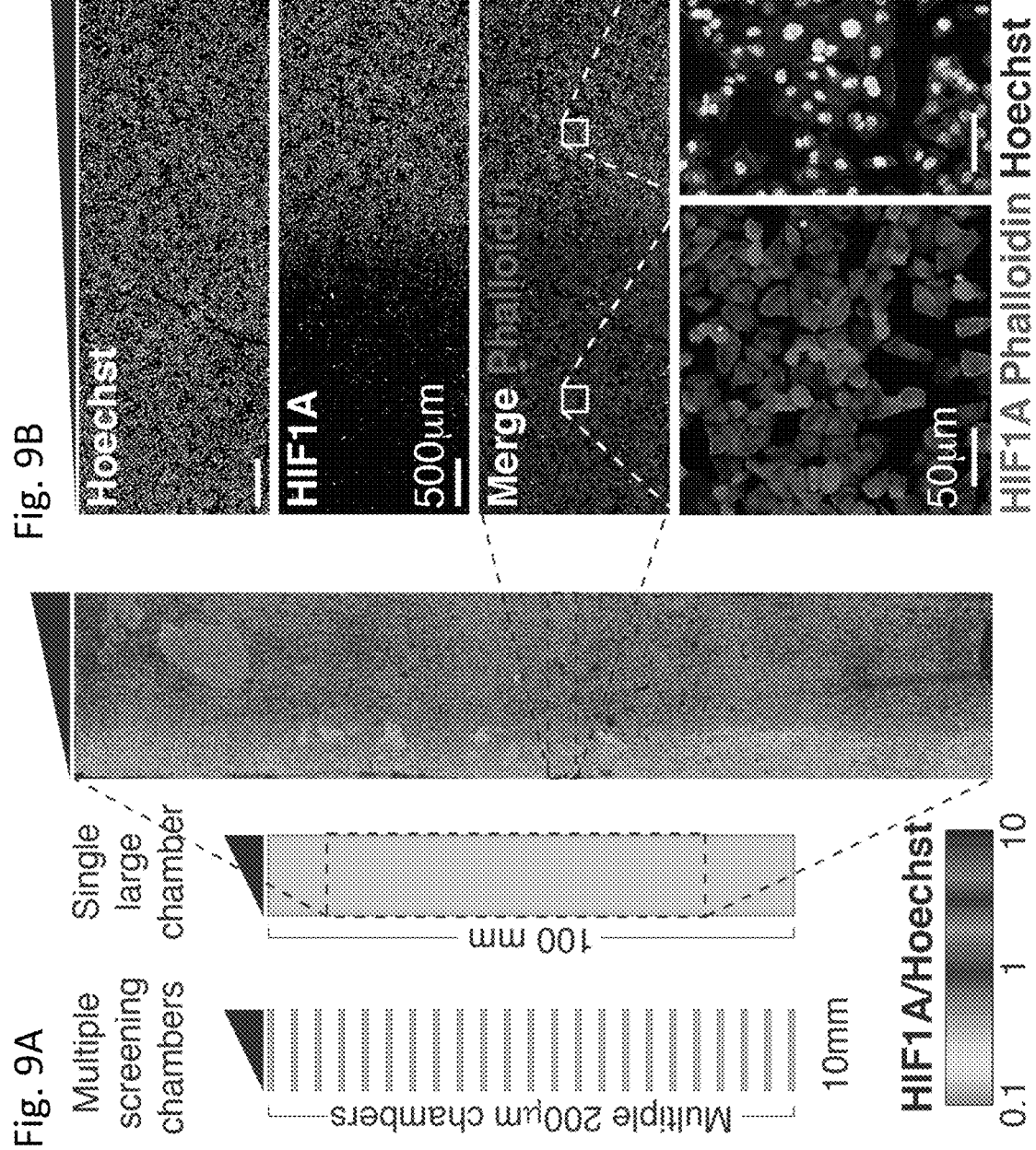

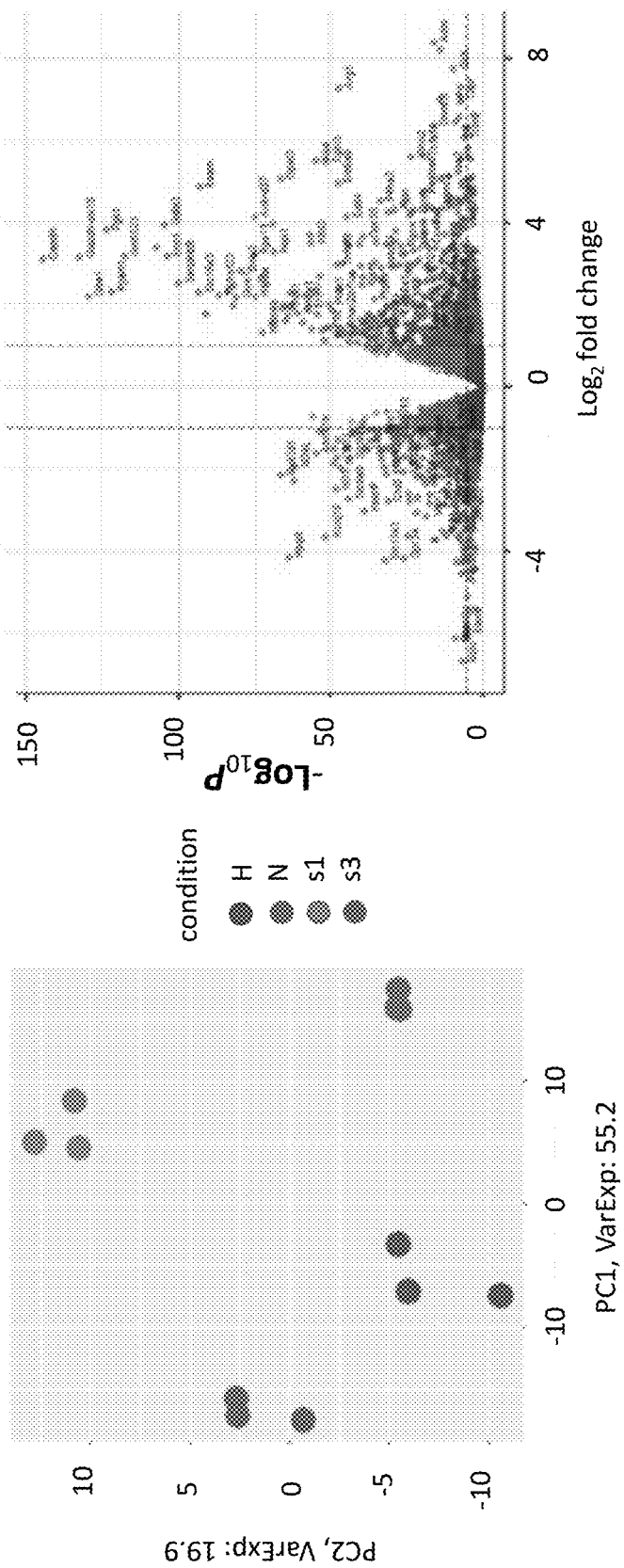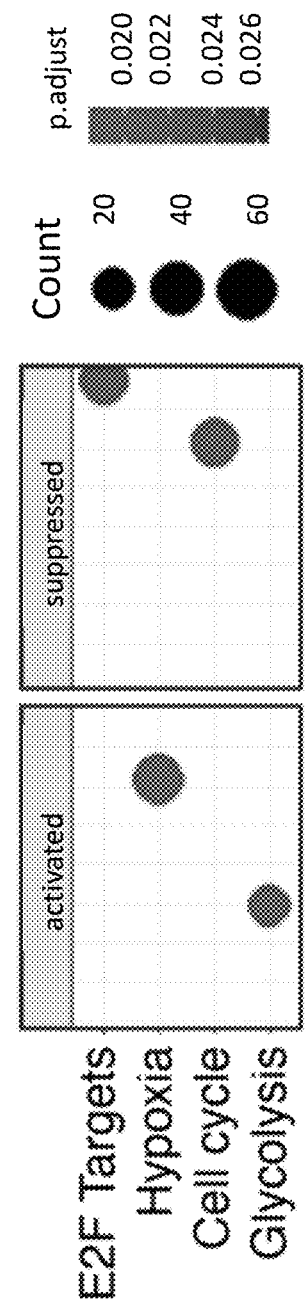
Fig. 11A
Fig. 11B
Fig. 11C

DISCRETE MICROENVIRONMENT CHAMBER

CROSS-REFERENCE TO RELATED APPLICATIONS

This application claims priority to U.S. Provisional Patent Application No. 63/127,485 filed Dec. 18, 2020, the contents of which are incorporated by reference herein in its entirety.

STATEMENT REGARDING FEDERALLY SPONSORED RESEARCH OR DEVELOPMENT

This invention was made with government support under R00CA191021 awarded by the National Institutes of Health. The government has certain rights in the invention.

BACKGROUND OF THE INVENTION

Insufficient blood perfusion is a hallmark, cause, and consequence of many pathologies including cancer, vascular stroke, viral infections, and neurodegenerative diseases (FIG. 1). This pathological lack of resources is known as tissue ischemia. For example, oxygen and nutrient deprivation caused by vascular strokes produce cell death, excessive inflammation, and other undesirable cellular changes that can have dire consequences on patient's health. Similarly, the exacerbated rate of cell growth in tumors leads to vascular insufficiency and to multiple regions with poor blood perfusion. While bad for the patient, these harsh conditions can benefit the tumor because these poor environments select for more resistant—and more malignant—tumor clones. Additionally, ischemic tumor cells often have metabolic adaptations that make them more resistant to conventional drug therapy. Finally, the lack of blood perfusion hampers the infiltration and suppress the function of tumor-killing immune cells and drug delivery.

Understanding how ischemic conditions affect cells at molecular level will provide opportunities to design novel therapeutics. Unfortunately, studying these cells within their native context is extremely difficult. In vivo experiments are often prohibitively expensive, and they require the destruction of the tissue microarchitecture, which comes at the cost of losing the critical information about the environment where cells reside. On the other hand, conventional in vitro experiments cannot accurately mimic ischemic conditions and other complexities of diseased organs and tissues.

Thus, there is a need in the art to develop experimental models that recreates key features of the tissue microenvironment and that allows to sample cells and media for biochemical analysis while retaining the environmental conditions. The present invention meets this need.

SUMMARY OF THE INVENTION

In one aspect, the present invention provides a discrete microenvironment chamber (DIMIC) device comprising: a chamber having a bottom layer, two sidewalls, a first end wall, a second end wall and a top plate, wherein the bottom layer is connected to the two sidewalls, the first end wall and the second end wall at peripheral edges, and wherein the first end wall comprises at least one opening positioned between the bottom layer and the top plate; and at least one port extending outward from the first end wall, wherein the at least one port is fluidly connected to the at least one opening.

In one embodiment, the distance between the first end wall and the second end wall ranges approximately between about 1-100 mm. In one embodiment, the distance between the two sidewall ranges approximately between about 1-300 mm. In one embodiment, the top plate is positioned parallel and above the bottom layer, connected to the two side walls and the first end wall and creates an opening with respect to the second end wall and a small gap between the top plate and the bottom layer.

In one embodiment, the opening has a width ranging approximately between about 1-100 mm. In one embodiment, the height of the small gap ranges approximately between about 0.1-20 mm.

In one embodiment, the first end wall comprises at least two openings, wherein the distance between the at least two openings ranges approximately between about 0.05-10 mm. In one embodiment, the at least one opening has a diameter ranging approximately between about 0.1-10 mm.

In one embodiment, the at least one port has a length ranging approximately between about 1-50 mm. In one embodiment, the device comprises a plurality of ports and wherein the plurality of ports have the same length. In one embodiment, the device comprises a plurality of ports and wherein the plurality of ports each have different lengths creating a slanted design configured to allow the extraction of cells and media from different local environments of the chamber.

In one embodiment, the device further comprises one or more needles having: a first end positioned within the chamber; a second end positioned outside the chamber and a lumen therebetween, wherein the needle is configured to fit inside the at least one opening and the at least one port and is configured to transport fluid from within the chamber to a sample collection device or an analysis instrument.

In one embodiment, the device further comprises at least one cell tray positioned on the bottom layer. In one embodiment, the at least one cell tray completely covers the bottom layer. In one embodiment, the at least one cell tray covers portions of the bottom layer. In one embodiment, the at least one cell tray further comprises perforations that allows the at least one cell tray to be easily split into different sectors. In one embodiment, each sector is seeded with at least one population of cells. In one embodiment, the different sectors are placed next to each other on the bottom layer. In one embodiment, the different sectors are placed anywhere on the bottom layer.

In one aspect, the present invention provides a method of using the device described herein. In one embodiment, the invention provides a method of analyzing the effects of ischemia on a cell population. In one embodiment, the method comprises providing a device comprising a chamber having a bottom layer, two sidewalls, a first end wall, a second end wall and a top plate, wherein the bottom layer is connected to the two sidewalls, the first end wall and the second end wall at peripheral edges, and wherein the first end wall comprises at least one opening positioned between the bottom layer and the top plate; and at least one port extending outward from the first end wall, wherein the at least one port is fluidly connected to the at least one opening. In one embodiment, the method comprises introducing and culturing cells into the chamber, wherein cells are cultured on the bottom layer. In one embodiment, the method comprises using at least one port to extract cells and/or culture media from different local environments of the chamber.

BRIEF DESCRIPTION OF THE DRAWINGS

The following detailed description of invention will be better understood when read in conjunction with the appended drawings. It should be understood, however, that the invention is not limited to the precise arrangements and instrumentalities of the embodiments shown in the drawings.

FIG. 2A depicts a side view of an exemplary DIMIC. FIG. 2B depicts a perspective view of an exemplary DIMIC.

FIG. 4A depicts a top view of an exemplary DIMIC of the present invention. FIG. 4B depicts a transparent section of an exemplary DIMIC showing that plurality of ports are offset from each other to collect media across the entire gradient of ischemia.

FIG. 9A through FIG. 9B depict gradient formation in an exemplary DIMIC. FIG. 9A depicts a schematic showing examples of multiple small DIMICs (left) or single large DIMIC. FIG. 9B depicts immunofluorescent detection HIF1A—a master regulator of low oxygen response—show that gradients, even in large DIMICs are linear. This linearity allows separation of cells into discrete bins or sectors.

FIG. 11A through FIG. 11C depict RNA sequencing (RNAseq) analysis of macrophages cultured in the DIMIC device of the present invention. FIG. 11A depicts principal component analysis showing that the DIMIC device produces strong and distinct transcriptional changes. Replicates of macrophages extracted from sector 1 and 3 (normal and ischemic, respectively) cluster away from each other and from control environments (normoxia, N and hypoxia, H). FIG. 11B depicts a volcano plot comparing gene expression between normal and ischemic (S3) macrophages. FIG. 11C depicts GSEA analysis of transcriptional changes shown in FIG. 11B and highlighting pathways enriched in ischemic and normal macrophages.

DETAILED DESCRIPTION

Figure 1:
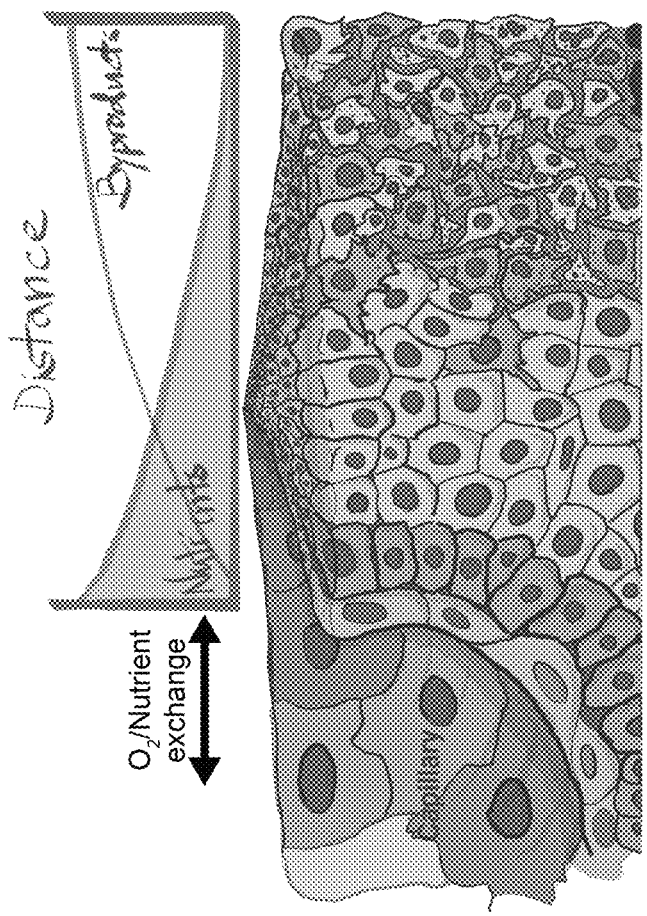
FIG. 1 depicts pathological tissues that are often heterogeneous with well-perfused cells residing nearby blood vessels and distal cells that are nutrient deprived or ischemic.

It is to be understood that the figures and descriptions of the present invention have been simplified to illustrate elements that are relevant for a clear understanding of the present invention, while eliminating, for the purpose of clarity many other elements found in the field of tissue ischemia. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Definitions

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Discrete Microenvironment Chamber (DIMIC)

The present invention provides a micro-physiological cell culture device configured to mimic local microenvironmental conditions. For example, in certain embodiments, the device mimics the conditions found within tumors and other pathologies in vivo. In one embodiment, the cell culture device of the present invention is able to accurately mimic the microenvironment of poorly perfused tissue.

In one embodiment, the cell culture device of the present invention produces local environmental changes via the same principles as in tissues, by allowing cells to be cultured in a small chamber that is connected to a large volume of fresh media through a small opening, wherein cells close to the opening are well perfused by culture media, while those distal to it become progressively more ischemic due to the diffusion and consumption/secretion of metabolites. In one embodiment, the design of this cell culture device is configured to produce local environmental changes via the same principles as in tissues and this gradients in the system accurately mimic pathological changes observed in vivo. In one embodiment, the cell culture device of the present invention is configured to allow extraction of cells and media from different local environments for any type of biochemical analysis. In one embodiment, the cell culture device of the present invention allows study of effects of tissue ischemia, in a wide range of pathological conditions, with unprecedented cellular and molecular resolution. In one embodiment, the cell culture device of the present invention is simple and yet is versatile, scalable, modular, and affordable.

Figure 2:
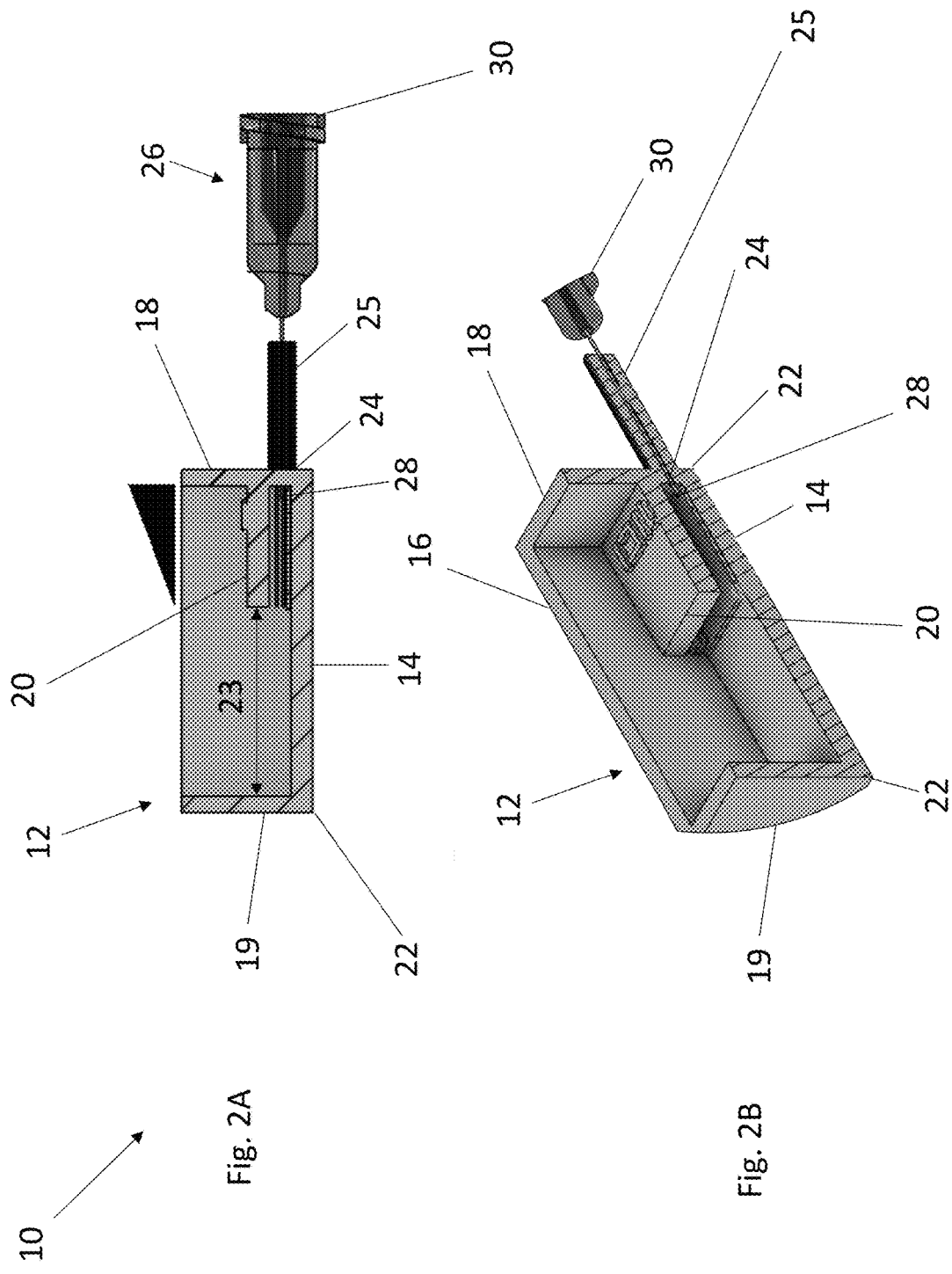
FIG. 2A through FIG. 2B depict an exemplary discrete microenvironment camber (DIMIC) of the present invention.
Figure 3:
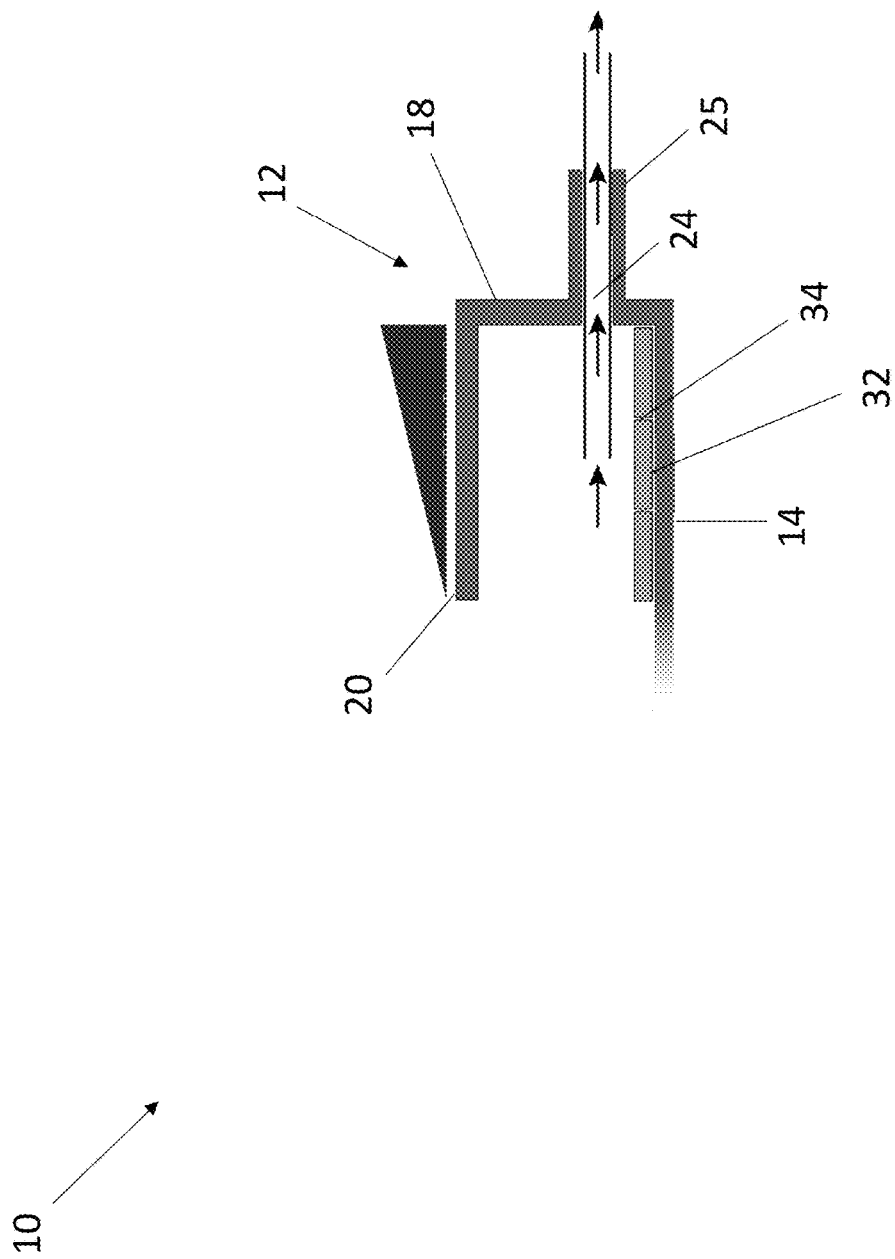
FIG. 3 depicts a side view of an exemplary DIMIC of the present invention.

Referring now to FIG. 2A, FIG. 2B and FIG. 3, an exemplary discrete microenvironment chamber (DIMIC) device 10 of the present invention is shown. Device 10 comprises a chamber 12 having a bottom layer 14, two sidewalls 16, a first end wall 18, a second end wall 19 and a top plate 20. Bottom layer 14 is connected to sidewalls 16, first end wall 18 and second end wall 19 at peripheral edges 22 to define chamber 12.

In one embodiment, chamber 12 may have a rectangular shape. In one embodiment, chamber 12 may have any other shapes known to one skilled in the art including but not limited to a cube, cylinder, a trapezoid, etc.

In one embodiment, chamber 12 may be made by any number of acceptable manufacturing methods well known to those of skill in the art. In one embodiment, chamber 12 may be assembled from a collection-of separately injection molded bottom layer 14, sidewalls 16, first end wall 18, second end wall 19 and top plate 20. In one embodiment, chamber 12 may be made from 3D printing. In one embodiment, chamber 12 may be made via methods including but not limited to laser-cutting technologies, traditional machining, etc.

In one embodiment, chamber 12 may be made from any material used or described for use in cell culture devices. In one embodiment, chamber 12 made be made from a material including but not limited to: glass, Polycarbonate (PC), polypropylene (PP), polyester (PE), polystyrene (PS), acrylonitrile butadiene styrene (ABS), Polylactic acid (PLA), and biocompatible resins for stereolithography. In one embodiment, chamber 12 may be made from a material that is gas permeable. In one embodiment, chamber 12 may be made from a material that is not gas permeable. In one embodiment, chamber 12 is disposable. In on embodiment, chamber 12 may be made from a material that can be sterilized between each use.

In one embodiment, chamber 12 may be made from a transparent material to allow easier accessibility and greater visibility of cells residing in chamber 12. In one embodiment, at least one of bottom layer 14, sidewalls 16, first end wall 18 and second end wall 19 may be made from a transparent material. In one embodiment, cells can be monitored from time to time by microscopic inspection through the generally transparent surfaces. Cells can be monitored for growth, differentiation, morphology, health, and the like.

In one embodiment, sidewalls 16, first end wall 18 and second end wall 19 have a height ranging between about 0.2-540 mm. In one embodiment, sidewalls 16, first end wall 18 and second end wall 19 may have the same height. In one embodiment, sidewalls 16 may be taller than first end wall 18 and second end wall 19. In one embodiment, sidewalls 16 may be shorter than first end wall 18 and second end wall 19. In one embodiment, the distance between sidewalls 16, defining the length of chamber 12, is between about 1 and 300 mm. In one embodiment, the distance between first end wall 18 and second end wall 19, defining the width of chamber 12, is between about 1-100 mm.

Figure 4:
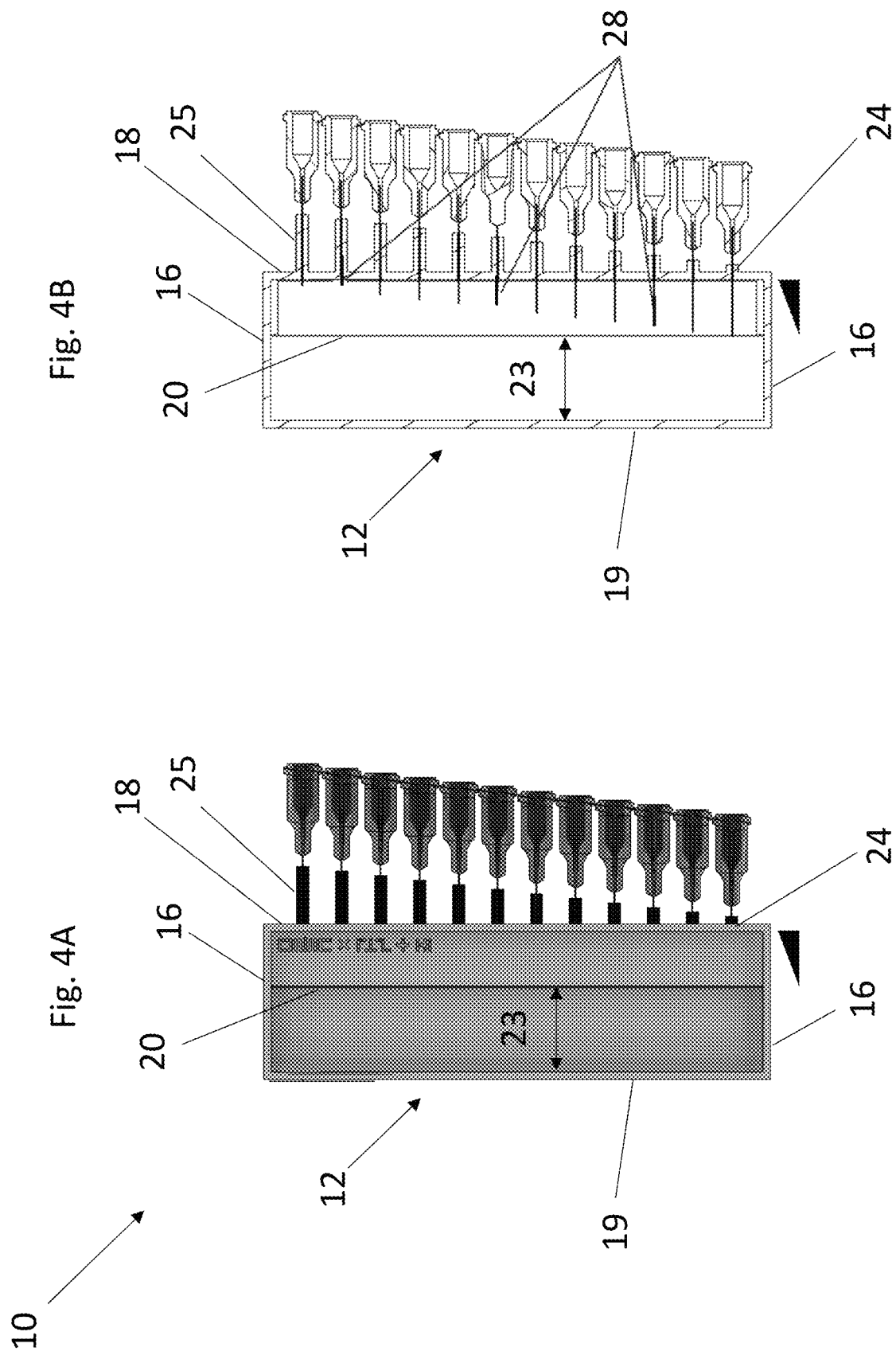
FIG. 4A through FIG. 4B depict a top view of an exemplary DIMIC of the present invention.

Referring now to FIG. 4, a top view of an exemplary device 10 of the present invention is shown. Top plate 20 is positioned parallel and above bottom layer 14, wherein top plate 20 is connected to two side walls 16 and first end wall 18 and creates an opening 23 between top plate 20 and second end wall 19 and a small gap 21 between top plate 20 and bottom layer 14. In one embodiment, opening 23 allows introduction and removal of media or any other components into chamber 12. In one embodiment, cells are cultured on bottom layer 14 and can be introduced into the chamber via opening 23. In one embodiment, cells cultured on bottom layer 14 and located under top plate 20 become progressively more ischemic due to the diffusion and consumption/secretion of metabolites as they get farther away from opening 23, whereas cells located close to opening 23 are well perfused by culture media. Because of this design, cells residing in device 10 experience local environmental changes via the same principles as in tissues and the gradient of ischemic conditions produced by device 10 accurately mimics pathological changes observed in vivo. In one embodiment, opening 23 has a width, spanning from second end wall 19 to top plate 20, between about 1-100 mm.

In one embodiment, top plate 20 has the same length as bottom layer 14. In one embodiment, top plate 20 may have a width ranging approximately between about 0.1-20 mm. In one embodiment, the height of gap 21 is ranging approximately between about 0.1-20 mm.

In one embodiment, first end wall 18 comprises at least one opening 24 positioned between bottom layer 14 and top plate 20. In one embodiment, the distance between two openings 24 may be ranging approximately between about 0.05-10 mm. In one embodiment, at least one opening 24 may have any appropriate cross-section including but not limited to circular, rectangular, square, etc. In one embodiment, at least one opening 24 may have a diameter ranging approximately between about 0.1-10 mm.

In one embodiment, at least one opening 24 is fluidly connected to at least one port 25 extending outward from first end wall 18. In one embodiment, at least one port 25 has a length ranging approximately between about 1-50 mm. In certain embodiments, the port can be connected via tubing (of any length) to an analytical machine or pump. In one embodiment, at least one port 25 has the same diameter as at least one opening 24. In one embodiment, at least one port 25 may have a larger diameter than at least one opening 24.

In one embodiment, device 10 may further comprise one or more needles 26 having a first end 28, a second end 30 and a lumen therebetween, wherein the needle is configured to fit inside at least one port 25 and go through at least one opening 24. In one embodiment, one or more needle 26 is configured to create a seal between chamber 12 and the environment. First end 28 is positioned within chamber 12 and is configured to allow a user to extract media or any other component without disrupting the environment (sampling). In one embodiment, first end 28 may also be used for medium sampling, medium replacement, injections of drug/compound dosing, physiologic and set-point monitoring, quality assurance data collection, perfusion, insertion of measuring probes, etc. In one embodiment, one or more needles 26 may be replaced with any other structure including but not limited to a tubing, to allow fluid transportation from chamber 12 without disrupting the environment.

Second end 30 extends toward outside of chamber 12 and is configured to transport the fluid from chamber 12 to a sample collection device or an analysis instrument. In one embodiment, second end 30 may have luer fittings to allow easier connection for sample extraction.

In certain embodiments, one or more needles 26 are configured such that the first end 28 of each needle 26 is positioned at different spatial locations within chamber 12. For example, in one embodiment, each first end 28 is inserted at a unique depth within chamber 12, thereby allowing for media sampling at various locations along the width and length of chamber 12. The insertion at various depths can be brought about by having needles of various lengths, or by having ports of various lengths, as described below.

In one embodiment, device 10 may comprise one or more ports 25. In one embodiment, ports 25 have the same length. In one embodiment, different length needles 26 may be inserted within ports 25 to allow a slightly offset design of needles 26 from each other. In one embodiment, ports 25 have different lengths, such that when needles 26 are inserted, a slightly offset design is provided.

This slanted design allows sampling from different locations within chamber 12. In one embodiment, this slanted design may be used to allow the extraction of cells and media from different local environments for any type of biochemical analysis. In one embodiment, the slanted design allows cells from different local environments within chamber 12 to be analyzed by flow cytometry, utilized in downstream analyses including bulk or single-cell RNA/DNA sequencing, proteomics, and metabolomics.

In one embodiment, device 10 further allows automated sampling capability, wherein a fluidic pump is fluidly connected to second end 30. In one embodiment, a pump is connected through tubing or any other means of sterile fluid routing for transporting the fluid and sample to a sample collection device or an analysis instrument. In one embodiment, the pump may be any pump known to one skilled in the art including but not limited to a microfluidic peristaltic pump. In one embodiment, the fluid routing may be disposable to limit opportunities for cross-contamination.

In one embodiment, device 10 may further comprise a top cover. In one embodiment, top cover can be removed to allow medium or any other component to be conveniently added and removed, by either pouring or pipetting, to and from device 10. In one embodiment, access for medium can also be made in any number of ways common to cell culture devices, including by way of caps, septums, and tubes.

In one embodiment, in the event that a closed system is desired, device 10 can be configured with inlet and outlet tubes that can be connected to medium source and waste bags by way of a sterile tubing connection, using equipment such as that made by Terumo Medical Corp. (Somerset, N.J.). Septum configurations, or any other techniques known to those skilled in the art, can also be used to create a closed system.

Figure 5:
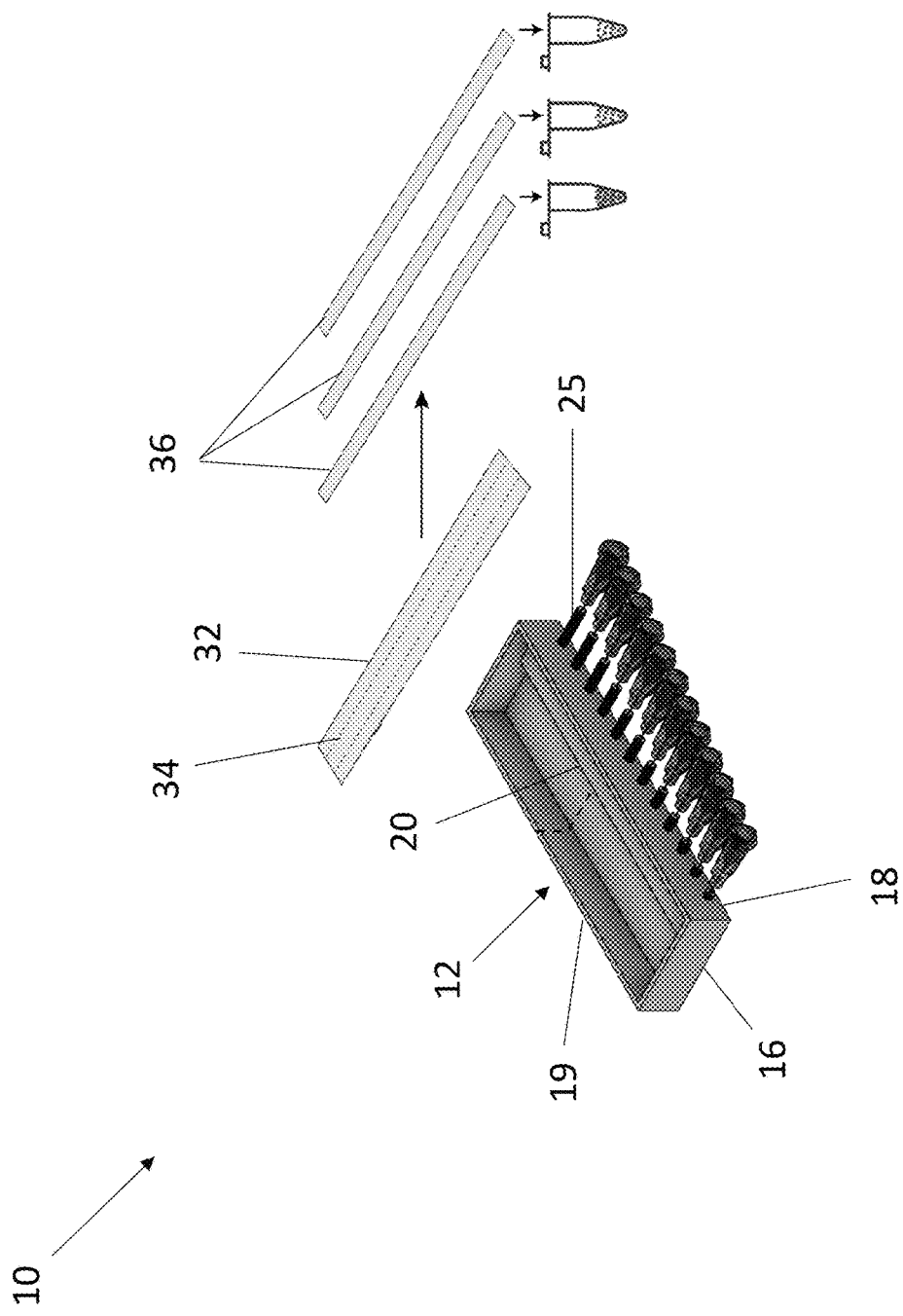
FIG. 5 depicts a perspective view of an exemplary DIMIC and cell trays of the present invention. In certain aspects, cells are collected from a laser-perforated removable cell tray. Perforations allow to easily split the tray into different regions that are processed separately.

Referring now to FIG. 5, a perspective view of an exemplary device 10 of the present invention is shown. In one embodiment, device 10 further comprises at least one cell tray 32, configured to allow culture of cells. In one embodiment, at least one cell tray 32 is positioned on bottom layer 14. In one embodiment, at least one cell tray 32 may have a width ranging approximately between about 0.1-20 mm. In one embodiment, at least one cell tray 32 may be positioned anywhere on bottom layer 14. In one embodiment, at least one cell tray 32 may fully cover bottom layer 14. In one embodiment, at least one cell tray 32 may cover only portions of bottom layer 14.

In one embodiment at least one cell tray 32 is a single unit, allowing for seeding of cells and/or collection of cells from the entirety of at least one cell tray 32. In one embodiment, at least one cell tray 32 may further comprise perforations 34 that allow at least one cell tray 32 to be easily split into a plurality of sectors 36. In one embodiment, each cell tray 32 may be split into at least two sectors 36. In one embodiment, each sector 36 may be seeded with at least one population of cells. In another embodiment, each sector 36 may be seeded with at least two different population of cells. In one embodiment, different sectors 36 of at least one cell tray 32 may be seeded with different population of cells. Under this configuration, different cell types are co-cultured within a shared environment that allows for cell-cell communication. In one embodiment, the end of the experiment, cells are extracted from different sectors 36 of at least one cell tray 32 allowing for cell type-specific downstream analyses that preserve the spatial information of each population. This unique feature can be used to study for example how ischemic immune cells affect the tumor and vice versa.

Figure 6:
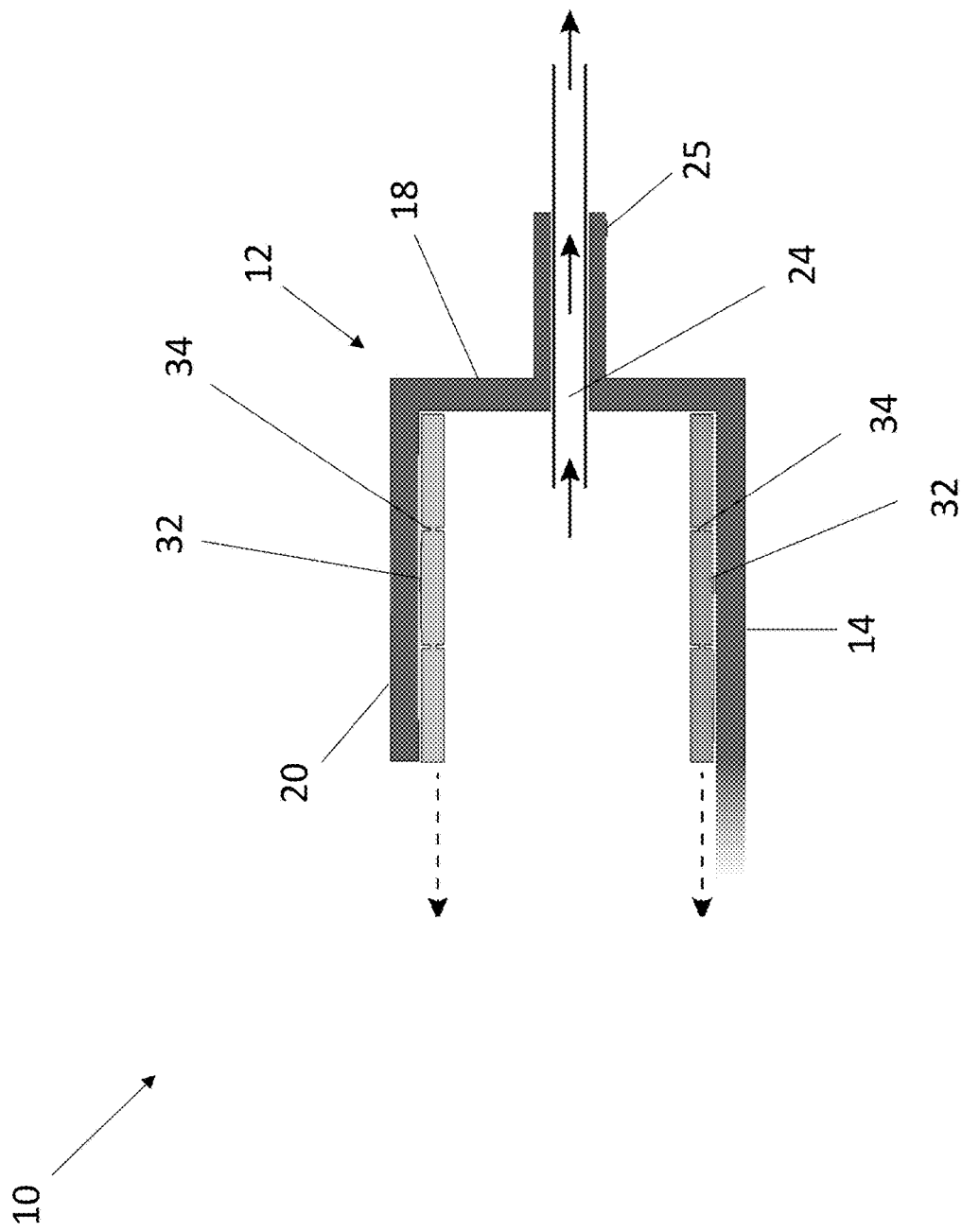
FIG. 6 depicts a side view of an exemplary dual DIMIC of the present invention. The exemplary dual DIMIC has two removable cell trays. This embodiment allows studying how different cell types interact retaining spatial information while allowing the deconvolution of different cell types.

In one embodiment, perforations 34 may be made using any method known to one skilled in the art including but not limited to a laser cutter. Perforations 34 allows different sectors of at least one cell tray 32 to be processed separately by the user. In one embodiment different sectors 36 may be placed next to each other on bottom layer 14. In one embodiment, different sectors 36 may be placed apart anywhere on bottom layer 14 (FIG. 6). In one embodiment, at least one cell tray 32 is removable.

In one embodiment, at least one cell tray 32 may be made from any material known to one skilled in the art including but not limited to glass, Polycarbonate (PC), polypropylene (PP), polyester (PE), polystyrene (PS), acrylonitrile butadiene styrene (ABS), Polylactic acid (PLA), and biocompatible resins for stereolithography In one embodiment, device 10 comprises a plurality of cell trays 32. For example, in one embodiment, device 10 comprises two cell trays 32. This embodiment allows studying how different cell types interact retaining spatial information while allowing the deconvolution of different cell types.

In one embodiment, any cell type can be used in device 10 including but not restricted to adherent and non-adherent cells, engineered cell lines, primary cells, and patient-derived cells. Device 10 can also use any kind of culture media, including common formulations as well as chemically defined and custom formulations. In one embodiment, fresh culture media can be replaced manually or replenished continuously with a simple perfusion system.

Cells may be isolated from a number of sources, including, for example, biopsies from living subjects and whole-organ recover from cadavers. In one embodiment, the isolated cells are autologous cells obtained by biopsy. The biopsy may be obtained using a biopsy needle, a rapid action needle which makes the procedure quick and simple.

Cells may be isolated using techniques known to those skilled in the art. For example, the tissue may be disaggregated mechanically and/or treated with digestive enzymes and/or chelating agents that weaken the connections between neighboring cells making it possible to disperse the tissue into a suspension of individual cells without appreciable cell breakage. Enzymatic dissociation may be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase and dispase. Mechanical disruption may also be accomplished by a number of methods including, but not limited to, scraping the surface of the tissue, the use of grinders, blenders, sieves, homogenizers, pressure cells, or sonicators.

Once the tissue has been reduced to a suspension of individual cells, the suspension may be fractionated into subpopulations from which the cells elements may be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting.

Cell fractionation may also be desirable, for example, when the donor has diseases such as cancer or metastasis of other tumors to the desired tissue. A cell population may be sorted to separate malignant cells or other tumor cells from normal noncancerous cells. The normal noncancerous cells, isolated from one or more sorting techniques, may then be used.

Isolated cells may be cultured in vitro to increase the number of cells available for seeding at least one cell tray 32. In one embodiment, allogenic cells or autologous cells may be used. In certain embodiments, chimeric cells, or cells from a transgenic animal, may be seeded onto at least one cell tray 32.

In certain embodiments, the cells can be stably or transiently modified using any method known in the art. For example, the cells can be modified to express a nucleic acid or protein of interest; or suppress the expression of a nucleic acid or protein of interest.

Isolated cells may be normal or genetically engineered to provide additional or normal function. Methods for genetically engineering cells with retroviral vectors, polyethylene glycol, or other methods known to those skilled in the art may be used. These include using expression vectors which transport and express nucleic acid molecules in the cells. (See Goeddel; Gene Expression Technology: Methods in Enzymology 185, Academic Press, San Diego, Calif. (1990). Vector DNA may be introduced into prokaryotic or cells via conventional transformation or transfection techniques. Suitable methods for transforming or transfecting host cells can be found in Sambrook et al. (Molecular Cloning: A Laboratory Manual, 3rd Edition, Cold Spring Harbor Laboratory press (2001)), and other laboratory textbooks.

In one embodiment, a range of 1 million to 50 million cells are suspended in medium and applied to each square centimeter of a surface of at least one cell tray 32 or bottom layer 14. at least one cell tray 32 or device 10 is incubated under standard culturing conditions, such as, for example, 37° C. 5% $CO_2$, for a period of time until the cells become attached. However, it will be appreciated that the density of cells seeded onto at least one cell tray 32 or bottom layer 14 may be varied. Other seeding techniques may also be used depending on the matrix or scaffold and the cells. For example, the cells may be applied to at least one cell tray 32 or bottom layer 14 by vacuum filtration. Selection of cell types, and seeding of cells onto at least one cell tray 32 or bottom layer 14, will be routine to one of ordinary skill in the art in light of the teachings herein.

In order to facilitate cell growth on at least one cell tray 32 or bottom layer 14, it may be coated with one or more cell adhesion-enhancing agents. These agents include but are not limited to collagen, laminin, and fibronectin.

Figure 7:
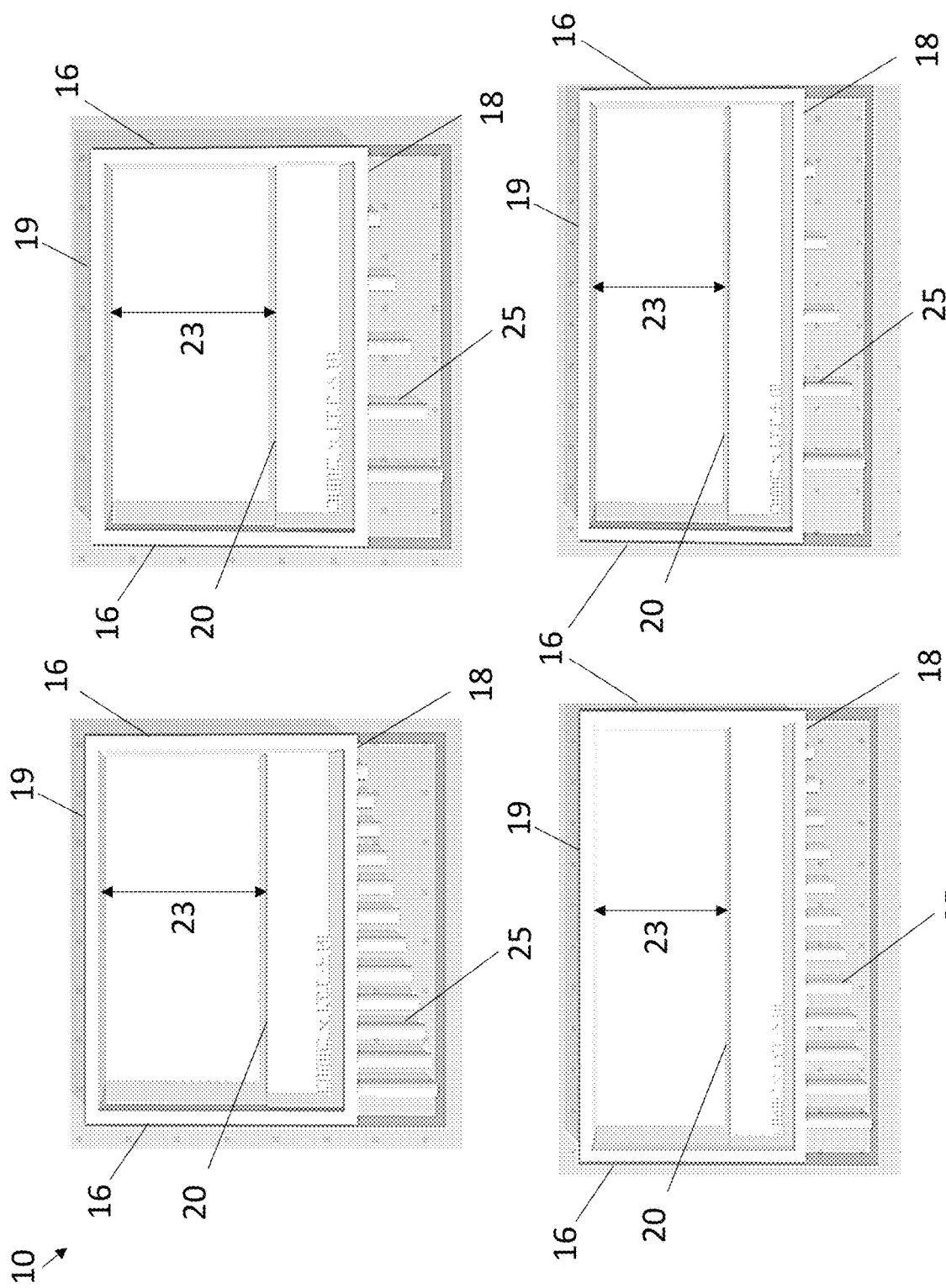
FIG. 7 depicts a top view of exemplary DIMIC of the present invention in various lengths, width, and number of ports.

Referring now to FIG. 7, a top view of several exemplary device 10 of the present invention is shown. In one embodiment, device 10 is easily scalable to the user's needs. In one embodiment, device 10 can be lengthened for experiments requiring large amounts of biomaterial including but not limited to CHIP-Seq experiments and whole genome CRISPR screens. In one embodiment, device 10 can be shortened into multiple tiny replicates (for example to few hundred microns each) to allow for multiplexing and screening experiments requiring numerous conditions and/or less biomass including but not limited to single-cell sequencing and image-based phenotypic screens.

In one embodiment, device 10 may be used for screening-based identification of novel therapeutic targets. In one embodiment, device 10 may be used for discovery and validation of disease biomarkers. In one embodiment, device 10 may be used for screening key genes/molecular players relevant to adapt and survive under ischemic conditions. In one embodiment, device 10 may be used for modeling the tumor microenvironment and study resistance to chemotherapy. In one embodiment, device 10 may be used in cancer immunotherapy. In one embodiment, device 10 may be used to study the effect of vascular stroke on neurons and brain damage. In one embodiment, device 10 may be used to study the effect of ischemia on tissue damage during viral infections. In one embodiment, device 10 may be used to study the role of inflammation on cell degeneration and tissue damage. In one embodiment, device 10 may be used to study the role of oxidative stress and other metabolic changes in drug resistance. In one embodiment, device 10 may be used to study the role of oxidative stress and DNA damage. In one embodiment, device 10 may be used to study metabolic immunosuppression during viral infection. In one embodiment, device 10 may be used to study the effect of the metabolic microenvironment on stem cell differentiation. In one embodiment, device 10 may be used to study regulation of tissue damage and regeneration.

Method of Use

The present invention relates to methods of culturing cells in a cell culture device configured to mimic local microenvironmental conditions. In one embodiment, the method of present invention allows culturing cells under different microenvironment. For example, in certain embodiments, the device mimics the conditions found within tumors and other pathologies in vivo. In one embodiment, the method of present invention allows extraction of cells and media from different local environments for any type of biochemical analysis.

Figure 8:
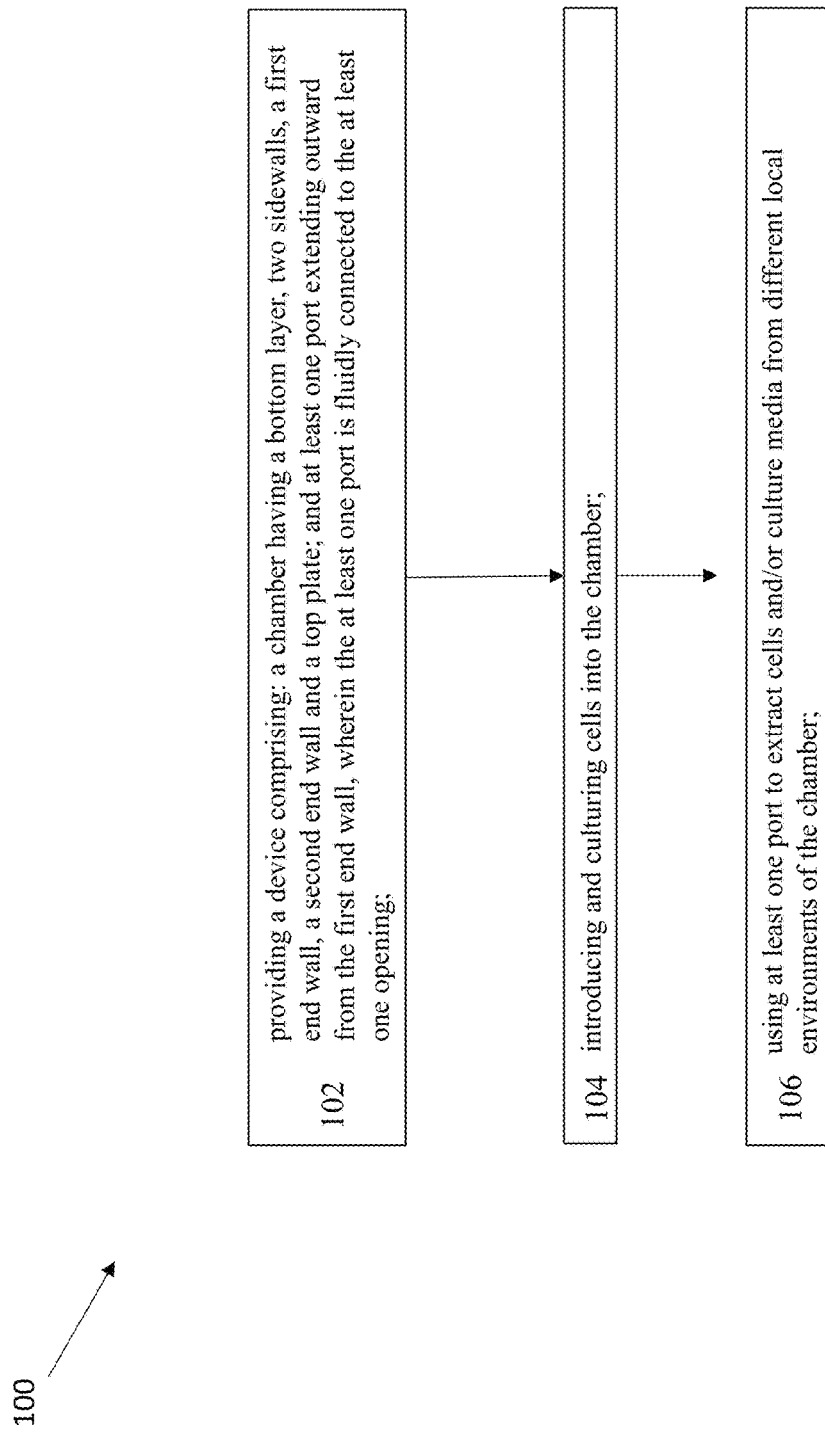
FIG. 8 is a flowchart depicting an exemplary method of using a DIMIC of the present invention.
Figure 10A:
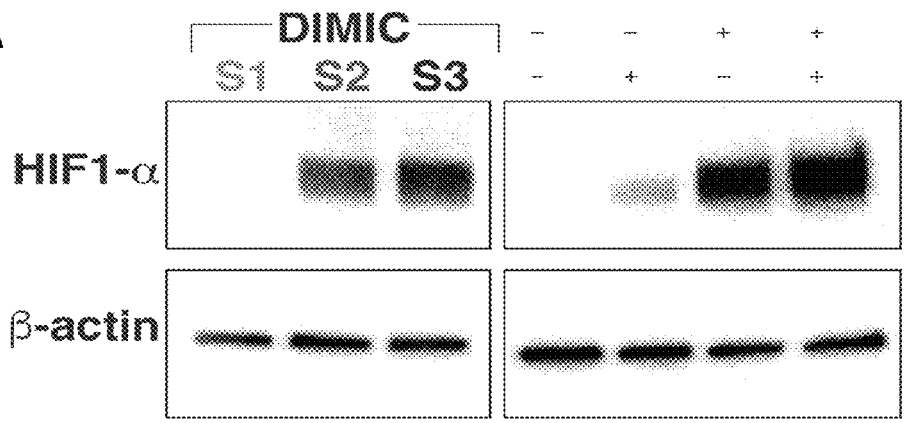
FIG. 10A through FIG. 10C depict molecular analysis of cells in an exemplary DIMIC. The removable tray was perforated for easy separation into 3 sectors: well-perfused, ischemic, and intermediate. Each sector was processed separated different replicates were used to detect proteins levels, mRNA expression, and intracellular metabolites. As expected, HIF1A protein is stabilized in more ischemic cells (FIG. 10). Typical HIF1A targets—including a GFP sensor expressed in engineered cells—were upregulated at the mRNA level (FIG. 10B). Ischemic cells showed increased level of metabolic byproducts such as lactate, increased levels of oncometabolites such as 2-Hydroxyglutatate (2-HG) and lower levels of glycolytic metabolites such as Fructose 1,6-biphosphate (Fructose-BP, FIG. 10C).
Figure 10B:
Figure 10C:
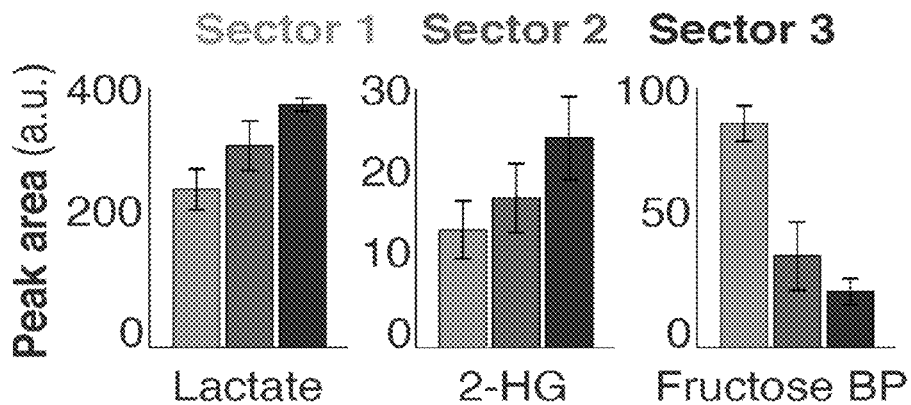

Referring now to FIG. 8, an exemplary method 100 of using the device of present invention is depicted. Method 100 begins with step 102, wherein a DIMIC device, as described elsewhere herein is provided. For example, in one embodiment, the DIMIC device comprises a chamber having a bottom layer, two sidewalls, a first end wall, a second end wall and a top plate. In one embodiment, the bottom layer is connected to the two sidewalls, the first end wall and the second end wall at peripheral edges. In one embodiment, the first end wall comprises at least one opening positioned between the bottom layer and the top plate. In one embodiment, the DIMIC device comprises at least one port extending outward from the first end wall, wherein the at least one port is fluidly connected to the at least one opening.

In step 104, cells are introduced to the chamber and cultured on the bottom layer. In one embodiment, the DIMIC device may further comprise at least one cell tray positioned on the bottom layer. In one embodiment, the at least one cell tray may completely cover the bottom layer. In one embodiment, the at least one cell tray may cover only portions of the bottom layer. In one embodiment, cells are cultured directly on the at least one cell tray.

In step 106, at least one port is used to extract cells and/or culture media from different local environments of the chamber. In one embodiment, the DIMIC device may further comprise one or more needles having: a first end positioned within the chamber; a second end positioned outside the chamber and a lumen therebetween, wherein the needle is configured to fit inside the at least one opening and the at least one port and is configured to transport fluid from within the chamber to a sample collection device or an analysis instrument. In one embodiment, extracted cells, cellular components (e.g, protein, RNA and DNA), and/or media are used for biochemical analysis. In one embodiment, cells may be extracted from the bottom layer or the at least one cell tray and used for analysis. For example, in one embodiment one or more of the at least one cell tray can be removed from the device. In one embodiment, cells may be taken from different part of the at least one cell tray, different parts of bottom layer, or different cell trays and used for analysis.

The cells, cellular components (e.g., proteins, DNA, and RNA), or media obtained from the device can be analyzed using any methodology known in the art. For example, cells can be stained and/or analyzed using immunofluorescence, immunocytochemistry, immunohistochemistry, or the like. In certain embodiments, the cells may be lysed to analyze protein expression, RNA expression, etc. Exemplary techniques used to analyze the cells or media obtained from the device includes, but is not limited to, DNA sequencing, RNA sequencing, PCR, RT-PCR, protein sequencing, immunoblotting, immunoprecipitation, ELISA, mass spectrometry, crystallography, and the like. Further, cells obtained from the device can further be subjected to one or more cellular assays to evaluate the function of the obtained cells. As a skilled artisan would readily understand, the present invention is not limited to any particular analysis, technique, or assay; but rather any suitable analysis, technique, or assay may be conducted on cells, media, or cellular components (e.g., proteins, DNA, and RNA) obtained from the device.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples, therefore, specifically point out the preferred embodiments of the present invention, and are not to be construed as limiting in any way the remainder of the disclosure.

Example 1: Discrete Microenvironment Chamber (DIMIC)

In vivo animal models are a fundamental tool in biomedical research. However, their use for large experiments is severely limited by practical, economical, and ethical reasons, such as husbandry costs and increasingly stricter regulations. In addition, the complexity of animal physiology—while crucial in clinical studies—can hamper experimental control and measurements in pre-clinical experiments that require testing multiple hypotheses. On the other hand, conventional in vitro experiments offer full experimental control, however they cannot capture essential features of the tissue microenvironment such as their intrinsic cellular and molecular heterogeneity. Thus, there is an urgent need to develop experimental models to complement the limitations of animal studies and in vitro cultures.

A key feature of multiple tissue pathologies is the presence of ischemic or poorly perfused tissues. The DIMIC offers a unique and cost-effective way to study how ischemia alters cell phenotypes and behavior. For example, it enables the study of how poor perfusion, alters tumor and immune cell functions in a physiologically relevant setting. One of the key advantages of this system is that it allows users to directly study how cells in distinct environments adapt and function in these conditions. As mentioned above, it is extremely difficult to study this within real tissues without losing crucial positional and environmental information. Furthermore, the DIMIC provides the user with the ability to obtain multi-parametric molecular data across a range of physiologically relevant metabolic environments, that would otherwise require multiple pieces of complex and expensive equipment that are not accessible to the general scientific community.

The main applications for the DIMIC are: 1) Screening-based identification of novel therapeutic targets. 2) Discovery and validation of disease biomarkers. 3) Screening of key genes/molecular players relevant to adapt and survive under ischemic conditions.

The DIMIC Device

The DIMIC is a micro-physiological ex vivo cell culture device that uses 3D-printing and laser-cutting technologies to mimic local conditions found within tumors and other pathologies in vivo.

As mentioned above, insufficient blood perfusion—or ischemia—is prevalent in multiple pathologies. In these affected tissues, ischemia is not a homogeneous but a gradual change that worsens with distance to the closest blood vessel (FIG. 1). These gradients are shaped by the diffusion of different molecules carried by the blood (e.g., oxygen, glucose) and by how fast cells consume these molecules. Conversely, metabolic by-products produced and secreted by cells—such as lactic acid—form reverse gradients that are also shaped by diffusion and by how fast cells secrete them (FIG. 1). Thus, changes in the tissue microenvironment have several features: 1) Environmental changes occur as linear gradients. 2) Gradients are complex where multiple analytes change simultaneously. 3) Cells have an active role in producing these gradients.

The DIMIC is a one-of-a-kind cell culture system that accurately mimics the microenvironment of poorly perfused tissue. Environmental changes in the DIMIC are generated by the same principles as they are in tissues and thus, they have homologous properties (i.e., complex linear gradients generated by cellular activities and diffusion). Importantly, the DIMIC was designed to allow the extraction of cells and media from different local environments for any type of biochemical analysis (FIG. 3). There is no other system that allow these kind of experiments analyses, and thus the DIMIC is a unique system to study effects of tissue ischemia, in a wide range of pathological conditions, with unprecedented cellular and molecular resolution.

The principle of the DIMIC is simple and yet this system is versatile, scalable, modular, and affordable. In this system, cells are grown on a removable tray within a small chamber that is connected to a large volume of fresh media through a small opening. This large volume acts as a source of nutrients and as a sink of metabolic byproducts (FIG. 3). Cells close to the opening are well perfused by culture media, while those distal to it become progressively more ischemic due to the diffusion and consumption/secretion of metabolites. Because of this design, cells in the DIMIC produce local environmental changes via the same principles as in tissues and this gradients in the system accurately mimic pathological changes observed in vivo.

The DIMIC allows sampling cells and media from different levels along the gradient of ischemia. To sample this material while retaining spatial information, the system separates the gradient of ischemia into discrete environmental bins (thus the name DIMIC).

For analysis of culture media, the DIMIC has several outlets where the user is able to extract small volumes of media without disrupting the environment. Each media-sampling port is located at a fixed location, but they are slightly offset from each other. This 'slanted' design ensures that the entire gradient of ischemia is covered by different ports (FIG. 2A, FIG. 2B, FIG. 4A, an FIG. 4B). Due to the small volume design, media is extracted at different time points—or even in a continuous manner using a microfluidics peristaltic pump. To analyze cells in the DIMIC, they are cultured on a tissue culture-treated tray that—thanks to perforations made using a laser cutter—easily splits into different 'sectors' that are processed separately at the end of an experiment (FIG. 5).

Users have virtually unlimited options of how to analyze cells and media extracted from the DIMIC. Cells are able to be re-cultured in new chambers, transferred to in vivo models, analyzed by flow cytometry, or utilized in downstream analyses including bulk or single-cell RNA/DNA sequencing, proteomics, and metabolomics (FIG. 9A and FIG. 9B). This system is also amenable to do large genetic screens such as whole-genome CRISPR/Cas9-based loss-of-functions. Similarly, extracted culture media is analyzed for changes in metabolites, cell signals, exosomes, DNA, etc. Users have virtually unlimited options of how to analyze cells and media extracted from the DIMIC. Cells are able to be re-cultured in new chambers, transferred to in vivo models, analyzed by flow cytometry, or utilized in downstream analyses including bulk or single-cell RNA/DNA sequencing, proteomics, and metabolomics (FIG. 9A and FIG. 9B). This system is also amenable to do large genetic screens such as whole-genome CRISPR/Cas9-based loss-of-functions. Similarly, extracted culture media is then analyzed for changes in metabolites, cell signals, exosomes, DNA, etc.

Versatility

In addition to this versatility when it comes to analysis, virtually any cell type can be used in the DIMIC including but not restricted to adherent and non-adherent cells, engineered cell lines, primary cells, and patient-derived cells. The DIMIC can also use any kind of culture media, including common formulations as well as chemically defined and custom formulations. Fresh culture media can be replaced manually or replenished continuously with a simple perfusion system.

Scalability

The DIMIC is easily scalable to the user's needs. With a small change in the 3D-printing parameters, the DIMIC is lengthened for experiments requiring large amounts of biomaterial such as CHIP-Seq experiments and whole-genome CIRSPR screens. Conversely, the system can be shortened into multiple tiny replicates (few hundred microns each) to allow for multiplexing and screening experiments requiring numerous conditions requiring less biomass such as single-cell sequencing and image-based phenotypic screens (FIG. 9A).

Modular Design

The DIMIC has a modular design that allows to increase or decrease the complexity of experiments as needed. In addition to the basic idea of modeling gradients of ischemia, features of tissues in vivo such as the presence of different cell types, an extracellular matrix, oscillating drug levels, and organoid-like 3D cultures, can be easily incorporated into the DIMIC. More complex DIMIC models are more accurate representations of the tissue microenvironment, but they are harder to analyze and de-convolve and thus they are more amenable for low- to mid-throughput experiments. Simpler models have less parameters, so they are better suited for large screens and high-throughput experiments.

Dual-DIMIC Variation

The DIMIC has a design feature that partially escapes this tradeoff between complexity and throughput. Its design allows for a dual-DIMIC variation where two removable trays facing each other are used instead of one (FIG. 6). Under this configuration, different cell types are co-cultured within a shared environment that allows for cell-cell communication. At the end of the experiment, cells are extracted from different trays allowing for cell type-specific downstream analyses that preserve the spatial information of each population. This unique feature can be used to study for example how ischemic immune cells affect the tumor and vice versa. While the use of more than two trays would be inconvenient, the dual-DIMIC allows studying interactions between an unlimited number of cells. For example, if users want to study the role of ischemia on neurons in the presence of microglial cells and astrocytes. Then, they can grow the cell of interest (in this case neurons) in one tray and the other two cell types in the second tray. By keeping the cell of interest in one tray, it can be processed without contamination from the other cell types. If needed, different cells can be alternated as cell of interest to obtain information from all cell types.

Affordability

Despite all these features, the DIMIC is affordable. The material costs of the microfabrication of single DIMIC are comparable with the costs of other commercially available cell culture systems. These costs would drop exponentially with larger productions. Other costs such as consumables and assembly time are also low. The DIMIC uses cell culture media efficiently and it does not require—although it can incorporate if desired—extracellular matrices that are often very expensive. The assembly of the DIMIC is straightforward and quick and thus it is also affordable in personnel time.

Example 2: RNA Sequencing (RNAseq) Analysis of Macrophages Cultured in the DIMIC The DIMIC device is configured to seamlessly integrate advanced biochemical and genomic techniques—while retaining information of the location of cells. To illustrate this feature, RNA sequencing (RNAseq) was conducted to determine transcriptional changes induced by different environments in the DIMIC on primary macrophages. A well-established protocol was used to differentiate murine bone marrow stem cells into macrophages and then approximately 5 million of the differentiated cells were seeded in the DIMIC device. After 48 hours these cells were extracted into 3 sectors: normal (proximal to the opening), intermediate, and ischemic (distal to the opening). Total mRNA from each of these sectors were then extracted and processed using widely used mRNA sequencing, and analysis pipelines. This conventional approach was used to highlight that the device of the present invention is capable of integrating existing techniques without major modifications and yet is capable of producing unique data sets.

As shown in FIG. 11, gene expression patterns of different macrophage subpopulations are distinct and follow expected trends such as enrichment of glycolysis and hypoxia-response genes while in ischemic macrophages, while normal and S1 macrophages show increases in cell cycle and proliferation-related genes. In addition, novel changes was found in signaling pathways that are under further investigation (not shown).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A discrete microenvironment chamber (DIMIC) device comprising:
    a chamber having a bottom layer, two sidewalls, a first end wall, a second end wall and a top plate, wherein the bottom layer is connected to the two sidewalls, the first end wall and the second end wall at peripheral edges, and wherein the first end wall comprises a plurality of openings positioned between the bottom layer and the top plate;
    a plurality of ports, each port extending outward a length from the first end wall, and fluidly connected to an opening of the plurality of openings, wherein the length of each port is different; and
    at least one removable cell tray, wherein the at least one removable cell tray further comprises perforations that allow the removable cell tray to be split into different sectors.

2. The device of claim 1, wherein the distance between the first end wall and the second end wall ranges approximately between about 1-100 mm.

3. The device of claim 1, wherein the distance between the two sidewall ranges approximately between about 1-300 mm.

4. The device of claim 1, wherein the top plate is positioned parallel and above the bottom layer, connected to the two side walls and the first end wall and creates an opening with respect to the second end wall and a gap between the top plate and the bottom layer.

5. The device of claim 4, wherein each opening of the plurality of openings has a width ranging approximately between about 1-100 mm.

6. The device of claim 4, wherein the height of the gap ranges approximately between about 0.1-20 mm.

7. The device of claim 1, wherein the distance between each opening of the plurality of openings ranges approximately between about 0.05-10 mm.

8. The device of claim 1, wherein the at least one each opening of the plurality of openings has a diameter ranging approximately between about 0.1-10 mm.

9. The device of claim 1, wherein each port of the plurality of ports has a length ranging approximately between about 1-50 mm.

10. The device of claim 1, wherein the length of each port increases incrementally along the first end wall.

11. The device of claim 1, wherein the device further comprises one or more needles having: a first end positioned within the chamber; a second end positioned outside the chamber and a lumen therebetween, wherein the needle is configured to fit inside an opening of the plurality of openings and a port of the plurality of ports and is configured to transport fluid from within the chamber to a sample collection device or an analysis instrument.

12. The device of claim 1, wherein the at least one removable cell tray completely covers the bottom layer.

13. The device of claim 1, wherein the at least one removable cell tray covers portions of the bottom layer.

14. The device of claim 1, wherein each sector is seeded with at least one population of cells.

15. The device of claim 1, wherein different sectors are placed next to each other on the bottom layer.

16. The device of claim 1, wherein different sectors are placed anywhere on the bottom layer.

17. A method of analyzing the effects of ischemia on a cell population comprising:
    providing a discrete microenvironment chamber (DIMIC) device comprising:
        a chamber having a bottom layer, two sidewalls, a first end wall, a second end wall and a top plate, wherein the bottom layer is connected to the two sidewalls, the first end wall and the second end wall at peripheral edges, and wherein the first end wall comprises a plurality of openings positioned between the bottom layer and the top plate;
        a plurality of ports, each port extending outward a length from the first end wall, and fluidly connected to an opening of the plurality of openings, wherein the length of each port is different; and
        at least one removable cell tray, wherein the at least one removable cell tray further comprises perforations that allow the removable cell tray to be split into different sectors;
    introducing and culturing cells into the chamber, wherein cells are cultured on the bottom layer;
    using at least one port to extract cells and culture media from different local environments of the chamber;
    removing the cell tray; and
    splitting the cell tray into different sectors for separate analysis of the cells located in each sector.

* * * * *